United States Patent [19]

Barsa et al.

[11] 4,349,663
[45] Sep. 14, 1982

[54] BIS(CYCLIC UREAS) MONOMER COMPOSITIONS USEFUL IN MAKING POLYURETHANE POLYMERS

[75] Inventors: Edward A. Barsa, East Haven; Chung-Yuan Lin, Northford; Fred A. Stuber, North Haven, all of Conn.

[73] Assignee: The Upjohn Company, Kalamazoo, Mich.

[21] Appl. No.: 205,632

[22] Filed: Nov. 10, 1980

[51] Int. Cl.$^3$ .................. C08G 73/00; B01J 31/04; B01J 27/14; B01J 27/24; B01J 31/12; C07D 401/06; C07D 401/10; C07D 403/06
[52] U.S. Cl. ........................ 528/367; 528/45; 528/48; 528/58; 528/368; 544/296; 548/318
[58] Field of Search ............... 260/239.3 R; 548/318; 544/296; 564/59; 528/367

[56] References Cited

U.S. PATENT DOCUMENTS 4,138,398 2/1979 Richter et al. .................. 260/239.3

Primary Examiner—Natalie Trousof
Assistant Examiner—Frederick W. Pepper
Attorney, Agent, or Firm—Denis A. Firth; John Kekich

[57] ABSTRACT

Bis(cyclic ureas) are disclosed which have the formula

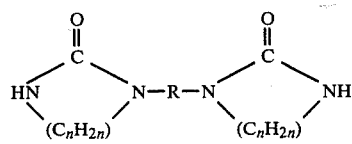

wherein R is

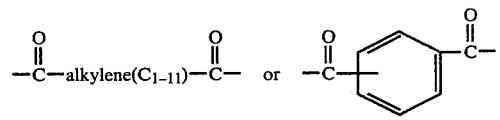

and $C_nH_{2n}$ is ethylene or 1,3-propylene each of which can be substituted by one or more inert substituents.

These compounds are useful as masked diisocyanates which, on heating in the presence of a polyol and, optionally, a polyurethane catalyst, give rise to polyurethane resins. Accordingly, they are useful as a component of storage stable compositions which are convertible to polyurethanes upon heating. Such compositions are particularly useful as solvent-less coating compositions. The properties of the above compounds are distinguished in a number of respects from the known bis(cyclic ureas) in which $C_nH_{2n}$ has 4 or more carbon atoms in the chain between the valencies. Illustratively, the above compounds are more stable on exposure to heat in the absence of catalysts but, in the presence of polyurethane catalysts, react with polyols at a significantly faster rate than the prior art compounds.

15 Claims, No Drawings

BIS(CYCLIC UREAS) MONOMER COMPOSITIONS USEFUL IN MAKING POLYURETHANE POLYMERS

BACKGROUND OF THE INVENTION

1. Field of the Invention

This invention relates to the preparation of novel heterocyclic compounds and compositions containing them and, more particularly, is concerned with the preparation of bis(cyclic ureas) which can act as masked diisocyanates, with stable one-component polyurethane forming systems containing said bis(cyclic ureas), and with processes for preparing polyurethane therefrom.

2. Description of the Prior Art

U.S. Pat. No. 4,138,398 discusses the applicable prior art (not repeated herein in the interest of brevity) and discloses a series of bis(cyclic ureas) having the following formula:

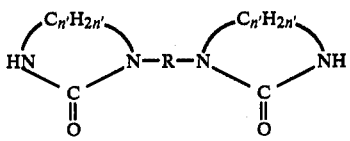  (I)

in which $C_{n'}H_{2n'}$ represents alkylene from 4 to 12 carbon atoms, inclusive, and in which there are at least 4 carbons in the chain separating the two N atoms and R is a divalent radical represented by

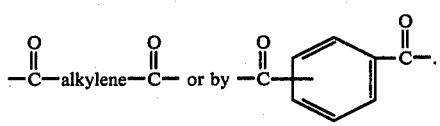

The compounds (I) are shown to function as masked diisocyanates in that, upon heating to temperatures of 100° C. or higher, they undergo ring opening to form the corresponding diisocyanate of the formula $$OCN-C_{n'}H_{2n'}-NH-R-NH-C_{n'}H_{2n'}-NCO \qquad (II)$$

where R and $C_{n'}H_{2n'}$ have the meaning defined above.

Because of this ability to generate a diisocyanate on heating, the compounds (I) are admixed with an appropriate polyol and employed as compositions which are stable on storage at ambient temperature (circa 25° C.) but which, upon heating to a temperature above that at which the compounds (I) undergo ring-opening, generate a polyurethane by reaction of the liberated diisocyanate with the polyol We have now found that compounds closely related to those of formula (I) above possess properties which are significantly different from those of formula (I) and these differences give rise to unexpected advantages in the use of the compounds of this invention as compared with the corresponding use of the compounds of formula (I).

SUMMARY OF THE INVENTION

This invention comprises bis(cyclic ureas) having the formula:

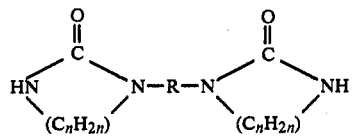  (III)

wherein R is a divalent radical selected from the class consisting of

  (a)

wherein alkylene contains from 1 to 11 carbon atoms, inclusive; and

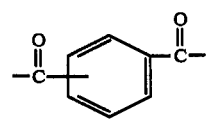  (b)

and $C_nH_{2n}$ is alkylene selected from the class consisting of

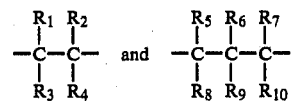

wherein $R_1$, $R_2$, $R_3$, $R_4$, $R_5$, $R_6$, $R_7$, $R_8$, $R_9$, and $R_{10}$ are each independently selected from the class consisting of hydrogen and an inert substituent.

The invention also comprises storage stable compositions which are adapted to generate polyurethane on heating which compositions comprise a compound of the formula (III), a polymeric polyol, and, optionally, a polyurethane catalyst.

The term "alkylene from 1 to 11 carbon atoms, inclusive" is inclusive of methylene, ethylene, propylene, butylene, pentylene, hexylene, heptylene, octylene, nonylene, decylene, undecylene and isomeric forms thereof.

The term "inert substituent" means a substituent which is chemically inert under the reaction conditions required to prepare the compounds (III) as hereinafter described. Exemplary of such substituents are:

alkyl such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and the like including isomeric forms;

alkenyl such as propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, and the like including isomeric forms;

aryl such as phenyl, tolyl, xylyl, naphthyl, diphenylyl and the like;

aralkyl such as phenethyl, benzyl, benzhydryl, phenylbutyl, naphthylmethyl and the like;

alkoxy such as methoxy, ethoxy, propoxy, butoxy, hexyloxy, nonyloxy, dodecyloxy, tetradecyloxy, octadecyloxy, nonadecyloxy, and the like including isomeric forms;

alkylmercapto such as methylmercapto, ethylmercapto, butylmercapto, hexylmercapto, octylmercapto, decylmercapto, tridecylmercapto, octadecylmercapto, nonadecylmercapto and the like including isomeric forms;

alkenyloxy such as propenyloxy, butenyloxy, hexenyloxy, nonenyloxy, dodecenyloxy, tetradecenyloxy, octadecenyloxy, nonadecenyloxy, and the like including isomeric forms;

aryloxy such as phenoxy, tolyloxy, xylyloxy, diphenylyloxy, naphthoxy and the like;

carbalkoxy, i.e. —COOAlkyl, wherein alkyl is above defined and exemplified;

haloalkyl, i.e. alkyl, as above defined and exemplified, which is substituted by one or more chloro, fluoro, bromo and or iodo groups;

haloaryl, i.e. aryl, as above defined and exemplified, which is substituted by one or more chloro, fluoro, bromo, and or iodo groups; and cyano;

While the $C_nH_{2n}$ group in the compound (III) can contain up to 4 (in the case of the 2 carbon atom chain) or up to 6 (in the case of the 3 carbon atom chain) inert substituents, it is found to be expedient that the total number of carbon atoms present does not exceed about 38.

DETAILED DESCRIPTION OF THE INVENTION

The compounds of the formula (III) are readily prepared by processes which are broadly known in the art; see, for example, the preparative methods described in the aforesaid U.S. Pat. No. 4,138,398. Illustratively the appropriate cyclic urea, of the formula

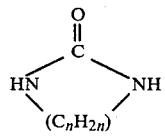

(IV)

wherein $C_nH_{2n}$ has the meaning defined above for formula (III), is reacted, in the presence of an inert organic solvent, with the appropriate diacid halide Hal-R-Hal wherein R has the meaning hereinbefore defined and Hal represents halogen (preferably chlorine or bromine). The reaction is carried out in the presence of a base such as an alkali metal hydroxide, tertiary amines and the like. The reaction conditions are described in detail in the aforesaid U.S. Pat. No. 4,138,398 and will not be repeated here.

The desired compound (III) is isolated from the reaction product using standard procedures. Illustratively, the salt formed by reaction of the base with the hydrogen halide eliminated in the condensation is removed by filtration or extraction with water and the organic solvent solution, after neutralizing any excess base, is evaporated to dryness. The compound (III), which remains as the residue, can be purified, if desired, by recrystallization, chromatography, and like techniques. In the case where the alkylene radical $C_nH_{2n}$ in the compounds (III) and (IV) is substituted by one or more inert substituents which is or are not symmetrically arranged the reaction product obtained by the process set forth above will be a mixture of isomers. This mixture can be separated into its component parts, if desired, by conventional techniques such as chromatography, fractional crystallization, and the like.

The cyclic ureas (IV) which are employed as starting materials to prepare the compounds (III) of the invention are, for the most part, known compounds and can be prepared by conventional procedures for the synthesis of cyclic ureas; see, for example, Ozaki et al., J. Amer. Chem. Soc., 79, 4358, 1957; see also the review by Peterson, Synthesis (International Journal of Methods in Synthetic Organic Chemistry), May 1973, pp. 243–292, which gives details of the preparation of cyclic ureas by a variety of methods and, at pages 271-2, gives a list of dihydro-2(1H)-pyrimidinones which can be subjected to catalytic hydrogenation using conventional techniques to yield the corresponding tetrahydro-2-(1H)-pyrimidinones. Illustrative of the compounds (IV) are the following, all of which are known in the art: 2-imidazolidinone; 4,4-dimethyl-,4,5-dimethyl-, 4-butyl-, 4-hexyl-, 4-propyl-, 4-(4-chlorophenyl)-, 4,5-diethoxy-, 4,5-dimethoxy-, 4,5-dibutoxy-, 4,5-diphenyl-, 4-methoxy-4,5,5-trimethyl-, 4,5-bis(dodecylthio)-, and 4-(2-naphthyl)-2-imidazolidinones; 3,4,5,6-tetrahydro-2(1H)pyrimidinone; 4-methyl-, 5-methyl-, 5,5-dimethyl-, 4,4,6-trimethyl-, 4-isopropyl-5,5-dimethyl-, 3-phenyl-, 3-phenyl-5-p-tolyl, 3-phenyl-5-p-chlorophenyl-, 3-phenyl-5-(2,6-dichlorophenyl)-, 4,6-diphenyl-, 4-methoxy-5,5-dimethyl-, 6-methoxy-5,5-dimethyl-4-isopropyl-, and 4-methoxy-5-methyl-3,4,5,6-tetrahydro-2(1H)pyrimidinones.

The compounds of the invention having the formula (III) are, surprisingly and unexpectedly, found to differ in properties from the closely related compounds, described in U.S. Pat. No. 4,138,398, which contain four or more carbon atoms in the chain separating the two nitrogen atoms in the heterocyclic rings and which have the formula (I) set forth above. Thus, the latter compounds undergo ring opening to form the corresponding diisocyanates (II) upon heating, in the absence of catalyst, to temperatures of about 100° C. or higher. In direct contrast, the compounds (III) of the invention do not undergo such ring opening when heated, in the absence of catalyst, to temperatures as high as 180° C. However, when the heating of the compounds is carried out in the presence of an active-hydrogen containing compound and a polyurethane catalyst, i.e. a catalyst which promotes the reaction between isocyanate groups and active-hydrogen containing groups, the reverse order of rates of reaction is found to exist. Thus, it is found that, under these circumstances, the compounds of the invention (III) readily undergo reaction to form the corresponding urethanes, whereas the prior art compounds, illustratively those having a 4-carbon atom chain (tetramethylene) between the N atoms in each ring, undergo the reaction at a significantly lower rate.

This difference in reactivity between the compounds of the invention of formula (III) and the corresponding compounds of the prior art having larger heterocyclic rings is highly advantageous in practical applications such as the formation of coating compositions utilizing these compounds. Illustratively, coating compositions prepared by dissolving stoichiometrically equivalent amounts of a polyether polyol and a compound of the invention ($C_nH_{2n}$=propylene-1,3; R=azelaoyl) together with a polyurethane catalyst in an inert organic solvent can be applied to a metal surface and the coated metal baked for a short period (1 hour) at 168° C. to give a coating which is fully cured and is insoluble in polar solvents such as methyl ethyl ketone. In direct contrast, when the procedure is repeated but the compound of the invention is replaced by a compound which differs therefrom only in the replacement of the propylene-1,3chain by tetramethylene-1,4, the resulting coating, even after baking for the same period of time and at the same temperature as the previous coating, is completely soluble in methyl ethyl ketone due to the much slower, and incomplete, polymer forming reaction which has taken place.

Other practical advantages which flow from the above difference in properties between the compounds of the invention and the most closely related compounds of the prior art will be readily apparent to those skilled in the art. Thus, because the compounds of the invention are not converted by heat alone (i.e. without the use of a catalyst) to the corresponding diisocyanates, they can be stored in admixture with polyols over a wide range of temperature without the possibility that a polyurethane forming reaction will occur. Accordingly, the compounds of the invention can be utilized in storage stable compositions which can be readily converted at any required moment to a polyurethane by the addition of an appropriate polyurethane catalyst followed by heating of the mixture at a temperature in the range of about 100° C. to about 250° C. The closely related compounds of the prior art can also be stored in admixture with polyols and will not undergo reaction therewith provided the temperatures do not greatly exceed about 50° C. but such mixtures are subject to the tendency to undergo polyurethane forming reaction if subjected to higher temperatures during storage.

In spite of the latter tendency the mixtures containing the prior art bis(cyclic ureas) react to form polyurethanes at a markedly slower rate, even in the presence of a polyurethane catalyst, than do the mixtures in accordance with this invention. This surprising difference in rate of reaction, coupled with the much wider margin of temperature ranges at which mixtures of the compounds (III) and polyols can be stored without change for prolonged periods, makes the use of such compositions much more attractive, compared with the closely related prior art compositions, for use as coating compositions and the like in which uses the mixed reactants may be stored for long periods prior to application.

The storage stable compositions of the invention, which have the various advantages noted above, comprise a compound of the formula (III), or a mixture of two or more of said compounds, and a polymeric polyol in substantially stoichiometric proportions, i.e. in such proportions that the equivalents of isocyanate groups which would be formed by ring opening of the compound (III) are substantially equal to the equivalents of hydroxyl groups present in the polyol or any other active hydrogen containing compounds which may be present. The polymeric polyols employed can be any of the polyester polyols or polyether polyols known in the art and having an equivalent weight of about 30 to about 1500 or higher and an average functionality of from about 2 to about 8. Illustrative of such polymeric polyols are those set forth in U.S. Pat. Nos. 3,745,133, 3,423,344 and 4,190,599. Optionally, the storage stable compositions can also contain extenders such as low molecular weight glycols, diamines, amine alcohols and the like.

As discussed above, it is necessary to employ a polyurethane catalyst in order to generate a polyurethane from the mixture of compound (III) and polymeric polyol. This catalyst may be included in the mixture during storage or may be added thereto just prior to generating the polyurethane by heating. The presence of the catalyst during storage of the composition will tend to reduce the range of temperatures to which the composition can be exposed during storage and the addition of the catalyst just prior to generation of the polyurethane from the stored mixture may be the preferred operating procedure in certain cases.

Any of the polyurethane catalysts known in the art can be employed for the above purpose; see for example, Saunders et al., Polyurethanes, Chemistry and Technology, Part I, Interscience, New York, 1963, page 228-232; see also Britain et al., J. Applied Polymer Science, 4, 207-211, 1960. Such catalysts include organic and inorganic acid salts of, and organometallic derivatives of, bismuth, lead, tin, iron, antimony, uranium, cadmium, cobalt, thorium, aluminum, mercury, zinc, nickel, cerium, molybdenum, vanadium, copper, manganese and zirconium, as well as phosphines and tertiary organic amines. Representative organotin catalysts are stannous octoate, stannous oleate, dibutyltin dioctoate, dibutyltin dilaurate, and the like. Representative tertiary organic amine catalysts are triethylamine, triethylenediamine, N,N,N',N'-tetramethylethylenediamine, N,N,N',N'-tetraethylethylenediamine, N-methylmorpholine, N-ethylmorpholine, N,N,N',N'-tetramethylguanidine, N,N,N',N'-tetramethyl-1,3-butanediamine, N,N-dimethylethanolamine, N,N-diethylethanolamine, and the like. The amount of catalyst employed is generally within the range of about 0.02 to about 2.0 percent by weight based on the total weight of the reactants.

In order to convert the storage stable compositions of the invention to polyurethanes in the presence of the catalyst it is merely necessary to heat the composition containing the catalyst to a temperature in the range of about 100° C. to about 250° C. and preferably in the range of about 130° C. to about 190° C. The nature of the polyurethane obtained will obviously depend upon the nature of the polyol and any other active hydrogen containing materials which may be present in the composition. Thus, where the polyol is a glycol, with or without an extender present in the mixture, the resulting polyurethane will be elastomeric in nature. Where the polyol has more than two hydroxy groups in the molecule the resulting polyurethane will be crosslinked and generally solid and rigid.

The storage stable compositions of the invention may also have incorporated in them, at any appropriate stage of preparation, additives such as pigments, fillers, lubricants, stabilizers, antioxidants, coloring agents, fire retardants and the like which are commonly used in conjunction with polyurethane. The storage stable compositions can be used to prepare polyurethane coatings such as coatings for wire and other forms of metal (sheets, moldings and the like) and, depending on the polyol used, can be used to prepare sealants, gaskets, seals and the like. These coating applications can be conducted at elevated temperatures and generally do not require the use of solvent or the generation of any other volatile material or by-product.

The following examples describe the manner and process of making and using the invention and set forth the best mode contemplated by the inventors of carrying out the invention but are not to be construed as limiting.

EXAMPLE 1

N,N'-nonanedioyl-bis[3,4,5,6-tetrahydro-2(1H)pyrimidinone]

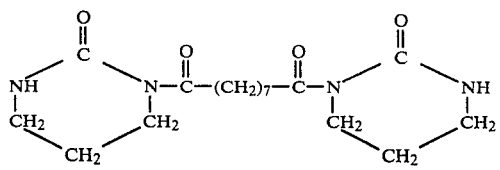

To a mixture of 27.5 g. (0.275 mole) of 3,4,5,6-tetrahydro-2(1H)pyrimidinone [ICN Pharmaceuticals Inc.] and 21.73 g. (0.275 mole) of pyridine in 350 ml. of methylene chloride was added dropwise, with stirring, a solution of 28.2 g. (0.125 mole) of azelaoyl dichloride in 150 ml. of methylene chloride. The addition was carried out at ambient temperature (circa 20° C.) and was complete in approximately 2 hours. After the addition had been completed, the resulting mixture was stirred for a further 3 hours at room temperature before being cooled in an ice-bath. The pyridine hydrochloride was removed by extraction with water and the resulting organic solution was dried over anhydrous calcium sulfate and evaporated to dryness. The residue (light brown solid) was recrystallized from trichloroethylene to obtain 35.6 g. (80.9 percent theoretical yield) of N,N'-nonanedioyl-bis[3,4,5,6-tetrahydro-2(1H)pyrimidinone] as a white crystalline solid having a melting point of 98° to 101° C.

Anal: Calcd. for $C_{17}H_{28}N_4O_4$: C, 57.93; H, 8.01; N, 15.90. Found: C, 58.00; H, 8.15; N, 15.37.

EXAMPLE 2

N,N'-isophthaloyl-bis[3,4,5,6-tetrahydro-2(1H)pyrimidinone]

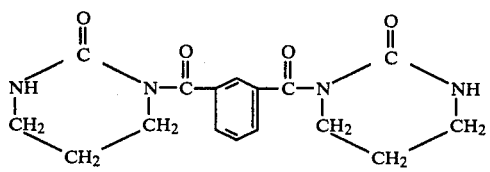

A mixture of 7 g. (0.07 mole) of 3,4,5,6-tetrahydro-2(1H)pyrimidinone and 8.6 g. (0.085 mole) of triethylamine in 500 ml. of benzene was stirred and heated under reflux and a solution of 5.1 g. (0.025 mole) of isophthaloyl dichloride in 50 ml. of benzene was added slowly over a period of 70 minutes. After the addition was complete, the heating under reflux and stirring was continued for a further 30 minutes. The resulting mixture was allowed to cool to room temperature (circa 20° C.) and the solid which had separated was removed by filtration. The solid so isolated was washed with three 100 ml. portions of boiling water giving 3.8 g. of the title compound. The combined hot water extracts were allowed to cool and the crystalline material which separated was isolated by filtration and dried. There was thus obtained 2.3 g. of N,N'-isophthaloyl-bis[3,4,5,6-tetrahydro-2(1H)pyrimidinone] having a melting point of 223° to 226° C. A third crop (1 g.) was obtained by concentration of the mother liquor.

Anal: Calcd. for $C_{16}H_{18}N_4O_4$: C, 58.17; H, 5.49; N, 16.96. Found: C, 57.75; H, 5.69; N, 16.80.

EXAMPLE 3

N,N'-nonanedioyl-bis[2-imidazolidinone]

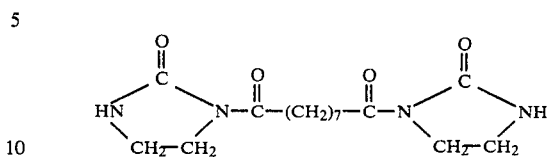

A mixture of 14.19 g. (0.165 mole) of 2-imidazolidinone and 13.05 g. (0.165 mole) of pyridine in 210 ml. of methylene chloride was stirred at room temperature (circa 20° C.) while a solution of 16.88 g. (0.075 mole) of azelaoyl dichloride in 90 ml. of methylene chloride was added slowly over a period of 3 hours. After the addition was complete, the mixture was stirred for a further 2 hours. The resulting mixture was allowed to cool to room temperature and was left to stand overnight. The product was filtered and the filtrate was neutralized by the addition of sodium hydroxide solution (12 g. of 50% w/w sodium hydroxide+9 ml. of water). The solid which separated was removed by filtration and the organic layer of the filtrate was isolated and evaporated to dryness. The residue was recrystallized from a mixture of carbon tetrachloride and chloroform and then from ethylene dichloride to give 11.5 g. of N,N'-nonanedioyl-bis[2-imidazolidinone]in the form of a white crystalline solid having a melting point of 125°–130° C.

EXAMPLE 4

N,N'-isophthaloyl-bis[2-imidazolidinone]

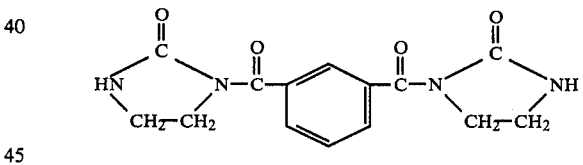

A suspension of 12.1 g. (0.14 mole) of 2-imidazolidinone (freshly recrystallized from chloroform) in 200 ml. of acetonitrile was heated to 80° C. and maintained thereat with stirring while a solution of 10.2 g. (0.05 mole) of isophthaloyl dichloride in 50 ml. of chloroform was added slowly over a period of 80 minutes. The resulting mixture was heated under reflux for a period of 3 hours. To the mixture was added slowly, over a period of 20 minutes, a solution of 11.11 g. (0.11 mole) of triethylamine in 20 ml. of chloroform. When the addition was complete, the product was heated under reflux for a period of 30 minutes before being cooled to 15° C. The solid which separated was isolated by filtration, washed on the filter with water (two 100 ml. portions of cold water and a 50 ml. portion of warm water) and dried at 70° C. overnight. There was thus obtained 9.26 g. (61.3 percent theoretical yield) of N,N'-isophthaloyl-bis[2-imidazolidinone].

Anal. Calcd. for $C_{14}H_{14}N_4O_4$: C, 55.62; H, 4.67; N, 18.54. Found: C, 55.55; H, 4.84; N, 18.49.

EXAMPLE 5

N,N'-isophthaloyl-bis(5,5-dimethyl-6-isopropyl-3,4,5,6-tetrahydro-2(1H)pyrimidinone) [mixture of isomers]

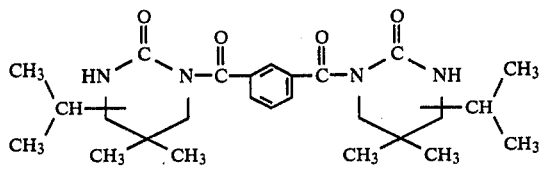

A mixture of 190 g. (1.1 mole) of 5,5-dimethyl-6-isopropyl-3,4,5,6-tetrahydro-2(1H)pyrimidinone (British Pat. No. 1,173,432) and 240 ml. (1.7 mole) of diethylamine in 3.4 liters of dichloroethane was heated to 70° to 75° C. and maintained thereat with stirring while a solution of 100 g. (0.5 mole) of isophthaloyl dichloride in 1 liter of dichloroethane was added dropwise over a period of 3 hours. After the addition had been completed the mixture was stirred for a short time and then cooled to room temperature (circa 20° C.) and washed successively with water, aqueous hydrochloric acid and aqueous sodium bicarbonate. The washed solution was dried over anhydrous sodium sulfate and then evaporated to dryness. The residue was extracted with 400 ml. of methanol and the extract was filtered to remove insoluble material. The methanol solution was diluted with 600 ml. of hot water. The solid which separated was isolated by filtration, washed on the filter with a mixture of 300 ml. of methanol and 450 ml. of water and then with a mixture of 100 ml. of acetone and 600 ml. of water. The washed solid was dissolved in methylene chloride and the solution was dried over anhydrous magnesium sulfate. The dried solution was evaporated to dryness to obtain 110 g. (50 percent theoretical yield) of a mixture of the isomers of N,N'-isophthaloyl-bis(5,5-dimethyl-6-isopropyl)-3,4,5,6-tetrahydro-2(1H)pyrimidinone).

Anal: Calcd. for $C_{26}H_{38}N_4O_4$: C, 66.64; H, 7.74; N, 11.96. Found: C, 66.24; H, 8.06; N, 11.14.

EXAMPLE 6

N,N'-terephthaloyl-bis[5,5-dimethyl-6-isopropyl-3,4,5,6-tetrahydro-2(1H)pyrimidinone) [mixture of isomers]

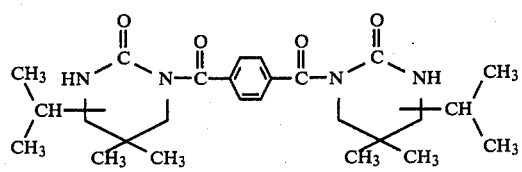

A mixture of 11 g. (0.064 mole) of 5,5-dimethyl-6-isopropyl-3,4,5,6-tetrahydro-2(1H)pyrimidinone and 11 ml. (0.078 mole) of triethylamine in 180 ml. of dichloroethane was heated under reflux with stirring and a solution of 6 g. (0.03 mole) of terephthaloyl chloride in 80 ml. of dichloroethane was added dropwise over a period of 90 minutes. The resulting mixture was cooled to room temperature (circa 20° C.) and washed successively with water, aqueous hydrochloric acid and aqueous sodium bicarbonate solution. The washed solution was dried over anhydrous sodium sulfate and evaporated to dryness. The residue was extracted with 100 ml. of methanol, the methanol solution was filtered and then treated with 150 ml. of water. The solid which separated was isolated by filtration, dissolved in methylene chloride and the solution was dried over anhydrous magnesium sulfate and evaporated to dryness. There was thus obtained 9.4 g. of a mixture of isomers of N,N'-terephthaloyl-bis(5,5-dimethyl-6-isopropyl-3,4,5,6-tetrahydro-2(1H)pyrimidinone) having a melting point of 150°-230° C.

Anal: Calcd. for $C_{26}H_{38}N_4O_4$: C, 66.64; H, 7.74; N, 11.96. Found: C, 66.30; H, 8.47; N, 11.70.

EXAMPLE 7

A comparison was made of the rates of reaction of the compound of Example 2 and the corresponding prior art compound having an additional methylene group in each heterocyclic ring. The two compounds correspond to the formula

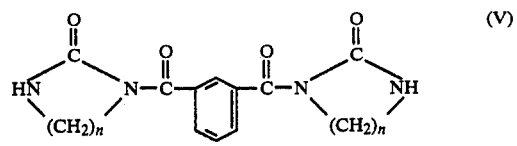

(V)

In the case of the compound of Example 2 the value of n is 3 in each ring. In the case of the prior art compound n=4 (see Example 1 of U.S. Pat. No. 4,138,398). The comparison of rates of reaction was carried out using the following standard procedure:

To a solution of 3 mmole of the test compound and 12 mmole of benzyl alcohol in 6 ml. of nitrobenzene was added 1 drop (0.015 mmole) of dibutyltin dilaurate. The resulting solution was then heated to a preselected temperature (see Table I below) and maintained thereat while the progress of the reaction was followed using nuclear magnetic resonance spectroscopy and observing the disappearance of the peak corresponding to the —$CH_2OH$ group and the appearance of the peak corresponding to the —$NHCOOCH_2$— group. The results so obtained are recorded in Table I which shows the percentage conversion to carbamate at the stated intervals after start of the heating period.

TABLE I

| Compound (IV) | Temp. °C. | % Conversion | | | | | |
|---|---|---|---|---|---|---|---|
| | | 0 min. | 5 min. | 10 min. | 15 min. | 20 min. | 30 min. |
| n = 4 | 155 | 10 | 50 | 70 | 80 | 91 | 100 |
| n = 3 | 155 | 55 | 90 | 100 | | | |
| n = 3 | 145 | 22 | 57 | 72 | N.T. | 81 | 92 |

It will be seen that, when both compounds were tested at 155° C., the rate of reaction of the compound of the invention (n=3 in formula V) is markedly greater than that of the prior art homologous compound (n=4 in formula V). Further, the compound of the invention when tested at the lower temperature 145° C. showed comparable rate of reaction to the prior art compound at 155° C.

EXAMPLE 8

Using exactly the same procedure as that described in Example 7, a comparison was made of the rates of reaction of the compound of Example 1 and the corresponding prior art compound having one additional methylene group in each heterocyclic ring. The two compounds correspond to the formula:

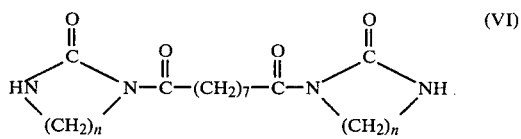 (VI)

In the case of the compound of Example 1 the value of n is 3 in each ring. In the case of the prior art compound the value of n is 4 (see U.S. Pat. No. 4,138,398). The results of the comparison are shown in Table II below.

TABLE II

| Compound VI | Temp. °C. | % Conversion | | |
|---|---|---|---|---|
| | | 0 min. | 15 min. | 30 min. |
| n = 4 | 160° C. | 15 | 86 | 100 |
| n = 3 | 160° C. | 26 | 100 | 100 |

It will be seen that the compound of the invention (n=3) reached 100 percent conversion at a significantly earlier time than the prior art compound (n=4). The effect of this difference in rates of reaction of the two compounds when employed in polyurethane forming reactions is illustrated in the example which follows.

EXAMPLE 9

Two solutions (A and B) were prepared by admixing the components shown in Table III below. Samples of the two solutions were coated on separate samples of sheet steel and the coated samples were baked for an hour at 168° C. At the end of the baking period the two films so obtained were cooled to room temperature and subjected to exposure to methyl ethyl ketone. It was found that the latter solvent did not effect the film prepared from solution A (containing the compound of the invention) whereas the film from solution B (containing the prior art compound) dissolved readily in the solvent. This difference indicated completion of the polyurethane forming reaction in the case of solution A but incomplete formation of the polymer in the case of solution B.

TABLE III

| | Solution A | Solution B |
|---|---|---|
| Compound VI (n = 3) | 0.9 g. (0.005 equiv.) | — |
| Compound VI (n = 4) | — | 0.98 g. (0.005 equiv.) |
| Polyol[1] | 1.18 g. (0.005 equiv.) | 1.18 g. (0.005 equiv.) |
| Dibutyltin dilaurate | 0.05 g. | 0.05 g. |
| Methyl cellosolve | 1 g. | 1 g. |

[1]Polyoxypropylene ether; functionality = 3, eq. wt. = 235.7 (Niax LHT 240; Union Carbide)

We claim:

1. A bis(cyclic urea) having the formula:

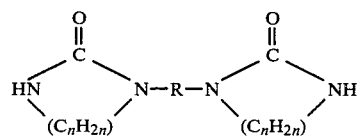

wherein: R is a divalent radical selected from the class consisting of

wherein alkylene contains from 1 to 11 carbon atoms, inclusive; and

and $C_nH_{2n}$ is alkylene selected from the class consisting of

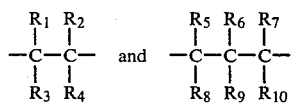

wherein $R_1$, $R_2$, $R_3$, $R_4$, $R_5$, $R_6$, $R_7$, $R_8$ $R_9$ and $R_{10}$ are each independently selected from the class consisting of hydrogen and an inert substituent.

2. A bis(cyclic urea) according to claim 1 wherein R is azelaoyl and $C_nH_{2n}$ in both instances is 1,3-propylene said compound being N,N'-nonanedioyl-bis[3,4,5,6-tetrahydro-2(1H) pyrimidinone].

3. A bis(cyclic urea) according to claim 1 wherein R is isophthaloyl and $C_nH_{2n}$ in both instances is 1,3-propylene said compound being N,N'-isophthaloyl-bis[3,4,5,6-tetrahydro-2(1H)pyrimidinone].

4. A bis(cyclic urea) according to claim 1 wherein R is isophthaloyl and $C_nH_{2n}$ in both instances is 3(or 1)isopropyl-2,2-dimethylpropylene-1,3 said compound being N,N'-isophthaloyl-bis[5,5-dimethyl-6(or 4)-isopropyl-3,4,5,6-tetrahydro-2(1H)pyrimidinone].

5. A bis(cyclic urea) according to claim 1 wherein R is terephthaloyl and $C_nH_{2n}$ in both instances is 3(or 1)isopropyl-2,2-dimethylpropylene-1,3said compound being N,N'-terephthaloyl-bis[5,5-dimethyl-6(or 4)-isopropyl-3,4,5,6-tetrahydro-2(1H)pyrimidinone].

6. A bis(cyclic urea) according to claim 1 wherein R is azelaoyl and $C_nH_{2n}$ is ethylene in both instances said compound being N,N'-nonanedioyl-bis[2-imidazolidinone].

7. A bis(cyclic urea) according to claim 1 wherein R is isophthaloyl and $C_nH_{2n}$ is ethylene in both instances said compound being N,N'-isophthaloyl-bis[2-imidazolidinone].

8. A storage stable composition adapted to form a polyurethane resin upon heating to a temperature in the range of about 100° C. to about 250° C. which composition comprises a mixture of:

(a) a bis(cyclic urea) having the formula:

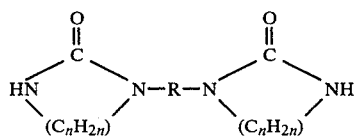

wherein R is a divalent radical selected from the class consisting of

wherein alkylene contains from 1 to 11 carbon atoms, inclusive; and

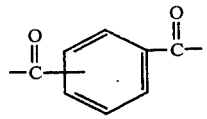

and $C_nH_{2n}$ is alkylene selected from the class consisting of

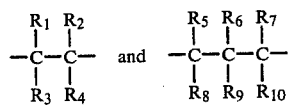

wherein $R_1$, $R_2$, $R_3$, $R_4$, $R_5$, $R_6$, $R_7$, $R_8$, $R_9$ and $R_{10}$ are each independently selected from the class consisting of hydrogen and an inert substituent; and (b) a polymeric polyol.

9. A composition according to claim 8 which also comprises a catalyst for the reaction of isocyanate groups with hydroxyl groups.

10. A storage stable composition according to claim 8 or 9 wherein the bis(cyclic urea) is N,N'-nonanedioyl-bis[3,4,5,6-tetrahydro-2(1H)pyrimidinone].

11. A storage stable composition according to claim 8 or 9 wherein the bis(cyclic urea) is N,N'-isophthaloyl-bis[3,4,5,6-tetrahydro-2(1H)pyrimidinone].

12. A storage stable composition according to claim 8 or 9 wherein the bis(cyclic urea) is N,N'-isophthaloyl-bis[5,5-dimethyl-6(or 4)-isopropyl-3,4,5,6-tetrahydro-2(1H)pyrimidinone].

13. A storage stable composition according to claim 8 or 9 wherein the bis(cyclic urea) is N,N'-nonanedioyl-bis[2-imidazolidinone].

14. A storage stable composition according to claim 8 or 9 wherein the bis(cyclic urea) is N,N'-isophthaloyl-bis[2-imidazolidinone].

15. A storage stable composition according to claim 8 or 9 wherein the bis(cyclic urea) is N,N'-terephthaloyl-bis[5,5-dimethyl-6(or 4)-isopropyl-3,4,5,6-tetrahydro-2(1H)pyrimidinone].

* * * * *

UNITED STATES PATENT OFFICE
CERTIFICATE OF CORRECTION

Patent No. 4,349,663                    Dated September 14, 1982

Inventor(s) Edward A. Barsa, Chung-Yuan Lin and Fred A. Stuber

It is certified that error appears in the above-identified patent and that said Letters Patent are hereby corrected as shown below:

Column 9, line 38 "-6-isopropyl)-" should read
-- -6-isopropyl- --. Column 10, Table I, line 46 "Compound IV" should read --Compound V--. Column 11, line 37 "effect" should read --affect--.

Signed and Sealed this

Seventh Day of December 1982

[SEAL]

Attest:

Attesting Officer

GERALD J. MOSSINGHOFF

*Commissioner of Patents and Trademarks*